United States Patent [19]

Garrett

[11] 4,139,487
[45] Feb. 13, 1979

[54] MIXED TRI-ARYL (PHENYL AND ALKYLPHENYL) PHOSPHATE ESTERS

[75] Inventor: Kenneth M. Garrett, Ottawa, Canada

[73] Assignee: Albright & Wilson Limited, Oldbury, England

[21] Appl. No.: 43,927

[22] Filed: Jun. 5, 1970

Related U.S. Application Data

[60] Division of Ser. No. 791,866, Jan. 6, 1969, Pat. No. 3,553,155, which is a continuation of Ser. No. 595,354, Nov. 18, 1966, abandoned.

[30] Foreign Application Priority Data

Dec. 1, 1965 [GB] United Kingdom ............... 51022/65

[51] Int. Cl.$^2$ .............................................. C07F 9/12
[52] U.S. Cl. ............................... 252/182; 252/78.5 R; 260/30.8 R; 260/966
[58] Field of Search .................... 252/182, 78.5 R; 260/30.6, 966, 30.6 R

[56] References Cited

U.S. PATENT DOCUMENTS

| | | | |
|---|---|---|---|
| 1,425,393 | 8/1922 | Laska et al. | 260/966 |
| 2,071,323 | 2/1937 | Bass | 260/966 |
| 2,168,587 | 8/1939 | Shuman | 260/30.6 |
| 2,182,817 | 12/1939 | Moyle | 260/966 |
| 2,193,252 | 3/1940 | Kyudes | 260/966 |
| 2,225,285 | 12/1940 | Moyle | 260/966 |
| 2,226,336 | 12/1940 | Cantrell et al. | 252/49.8 |
| 2,450,903 | 10/1948 | Mikeska | 260/966 |
| 2,636,861 | 4/1953 | Waston | 252/78.5 |
| 2,805,240 | 9/1957 | Prahl | 260/966 X |
| 2,868,827 | 1/1959 | O'Connor et al. | 260/975 |
| 2,960,524 | 11/1960 | Wilson | 260/975 |
| 3,028,410 | 4/1962 | Zimmer et al. | 260/968 |
| 3,071,549 | 1/1963 | Stark | 252/78.5 |
| 3,077,491 | 2/1963 | Seglin et al. | 260/975 |

FOREIGN PATENT DOCUMENTS

| | | |
|---|---|---|
| 532850 | 2/1922 | France. |
| 1262302 | 4/1961 | France. |
| 837679 | 6/1960 | United Kingdom. |
| 837680 | 6/1960 | United Kingdom. |
| 890642 | 3/1962 | United Kingdom. |
| 1146173 | 3/1969 | United Kingdom. |

OTHER PUBLICATIONS

Hackh's Chemical Dictionary, Fourth Edition, McGraw-Hill, New York, p. 187.
Dictionary of Organic Compounds, vol. 1 (1965) p. 521.
Buttrey, Plasticizers (1959), pp. 34, 35 & 175.
Mellan, Industrial Plasticizers, Pergammon Press, New York, (1963), pp. 209–211.
Modern Plastics Encyclopedia, vol. 43, No. 1A (1965) pp. 452 and 453.
Petzold, Technical Service Memo, No. 55 (Jun. 1944). 1944).
Kirk Othmer, Chem. Tech., vol. 10 (1953), pp. 766–798.
Bondy et al, J. Ind. Medicine, vol. 17 (1960), pp. 190–200.
Yokota et al, Chem. High Polymer Japan, No. 8 (1951) pp. 227–231.

Primary Examiner—Richard Raymond

[57] ABSTRACT

A composition consisting essentially of liquid mixed phenyl alkylphenyl phosphate having the average general formula $(RO)_3PO$ wherein from 30 to 85 mole-percent of the "R" group are secondary alkylphenyl groups, wherein the secondary alkyl group has from 3–4 carbon atoms, and the remaining "R" groups are phenyl groups. Flexible resin polyvinyl chloride polymers and copolymers incorporating said composition as the plasticizer therefor have improved cold flex characteristics.

19 Claims, No Drawings

MIXED TRI-ARYL (PHENYL AND ALKYLPHENYL) PHOSPHATE ESTERS

This invention relates to improved resin compositions and to certain plasticisers therefor.

It is common practice to plasticise many resin compositions containing polymers or copolymers of vinyl chloride to render them flexible. The plasticisers employed for this purpose are usually esters and the class of triaryl phosphate esters has been extensively employed for the purpose. Such phosphates have hitherto usually been prepared by esterification of various coal tar phenol fractions which may contain varying amounts of phenol, cresols and xylenols together with small amounts, not exceeding about 10% by weight, of higher alkylphenols, usually methyl-ethyl-phenols and diethylphenols. Such plasticisers have many advantages, but suffer from the major disadvantage that the plasticised compositions in which they are compounded tend to lose their flexibility at low temperatures.

It has now surprisingly been found that the presence of alkyl substituents of from 3 to 12 carbon atoms, especially the isopropyl and/or sec.-butyl group, in at least one of the aryl groups of the triaryl phosphate esters provides resin compositions which contain a polymer of vinyl chloride together with such esters as plasticisers with very satisfactory cold temperature flexibility, especially when compared with the case when other triaryl phosphates of corresponding molecular weight and derived from coal tar phenols are similarly employed. This comparison with compounds of corresponding molecular weight is appropriate since the usefulness of a plasticiser depends not only on the plasticising properties manifested, but also on the cost thereof and this latter point depends on the alkylphenols employed to prepare the plasticiser. Hitherto, the cold flex properties of polyvinyl chloride resin compositions containing triaryl phosphates prepared from coal tar phenols have left much to be desired. The improvement in cold temperature flexibility is manifested when only a modest proportion of the aryl groups, namely 20 mole-percent, possesses the $C_{3-12}$ alkyl substituent and indeed if each of the aryl groups possesses such a substituent the plasticiser may not be sufficiently compatible with the vinyl chloride polymer in the amounts in which it should be employed in order to achieve the desired plasticising effect.

Accordingly, the invention provides a resin composition comprising a polymer of vinyl chloride, and, a plasticiser therefor, a liquid triaryl phosphate prepared from one or more phenols and an ester-forming derivative of phosphoric acid, said phenols comprising at least 20 mole-percent, preferably 30–85 mole-percent, of alkylphenols possessing an alkyl substituent having from 3 to 12 carbon atoms, the plasticiser being present in an amount up to 150 parts by weight per 100 parts by weight of the resin as limited by the compatability of the phosphate ester and the polymer.

The most preferred triaryl phosphates for present use, that is those of the general formula $(RO)_3PO$, where each R represents a phenyl or alkylphenyl group wherein the alkyl substituent has up to 12 carbon atoms, characterised in that from 30 to 85 mole-percent of the R groups are isopropylphenyl and/or sec.-butylphenyl groups, are novel compounds and, accordingly, together with their preparation from a mixture of phenols, which comprises from 30 to 85 mole-percent of isopropylphenol and/or sec.-butylphenol, and an ester-forming derivative of phosphoric acid, constitute further aspects of the present invention.

By "triaryl phosphate" is included in the present context a mixture of separately prepared triaryl phosphates as well as a triaryl phosphate mixture prepared from a mixture of phenols. A mixture of separately prepared triaryl phosphates can, for present purposes, be deemed to be equivalent to a triaryl phosphate mixture prepared from such a mixture of phenols that it has a corresponding overall composition.

The present triaryl phosphate plasticisers wherein the aryl groups are identical are rarely used except in admixture with other triaryl phosphates since the tris-aryl phosphates having the necessary $C_{3-12}$ alkyl substituents in each aryl group are often incompatible with the resin when employed in the desired amount. Thus mixed phosphate esters or mixtures of phosphate esters are usually employed. These are preferably prepared by the reaction of an appropriate mixture of phenols with the esterforming derivative of phosphoric acid, preferably phosphorus oxychloride; but there may also be employed an appropriate blend of phosphate esters that have been separately prepared.

The alkylphenyl groups whose presence in the stated amount is the characteristic feature of the present plasticisers are those which contain at least one of the higher alkyl substituents, that is alkyl groups having from 3 to 12 carbon atoms, for example propyl, butyl, octyl, nonyl, decyl or dodecyl groups. Such alkylphenyl groups may also contain one or more methyl or ethyl substituents. Normally only one of the higher alkyl substituents is present, though more can be present if desired, and the use of phosphates containing a di-isopropyl-phenyl group according to the invention shows some promise. The higher alkyl substituent is preferably one having 3 to 7 carbon atoms especially an isopropyl, sec.-butyl, 2-pentyl, 2-hexyl or sec.-heptyl group, the presence of an isopropyl or sec.-butyl group being particularly advantageous. The presence of alkylphenyl groups which contain tertiary carbon atoms, as found for example in the tert.-octyl and 3,5,5-trimethylhexyl groups, is less preferred. However, mixtures of sec.-butylphenol and tert.-butylphenol may often be used without disadvantage. The positioning of the $C_{3-12}$ substituent or substituents relative to the phenolic hydroxyl group is not critical, though phosphate esters derived from ortho-substituted phenols are less preferred and the novel meta-isopropylphenyl phenyl phosphates appear to be the most preferred for present purposes.

The present plasticisers, however they may be obtained, can be considered as phosphate triesters of at least one alkylphenol possessing an alkyl substituent having from 3 to 12 carbon atoms, or more usually, of a mixture of phenols. In the latter instance at least 20 mole-percent of the mixture should consist of such $C_{3-12}$ alkylphenols. The remainder of the said mixture will consist of phenol, cresols and/or xylenols. Pure phenol may be used or it may be desirable to employ one of the mixtures of phenol, cresols and xylenols obtained from coal tar and known as coal tar phenol fractions. On the basis of cost and compatability of the phosphate ester with the resin, as well as in general providing the plasticised resin composition with an improved low temperature flexibility, it is preferred that between 30 and 85 mole-percent, particularly 30–50 mole-percent, of the mixture of phenols should consist of the said $C_{3-12}$ alkylphenols, such that the carbon number of the phosphate ester, that is the number of carbon atoms in the average general formula of the esters, is between 21 and 26, and more preferably between 21 and 24. When the non-higher alkylphenyl group in the phosphate ester themselves contain alkyl substituents, i.e. they are cresyl or xylyl groups, the mole-percentage of higher alkylphenol can in general be higher without disadvantage of insufficient compatability and lack of satisfactory improvement in cold flex temperature than when phenyl groups are present. Thus, when the non-higher alkyl groups in the phosphate ester are phenyl, it is preferred that the proportion of the higher alkylphenyl groups should not exceed 70 mole-percent. The preferred plasticisers for present purposes are those which correspond to the compounds mono(isopropylphenyl) diphenyl phosphate, mono-(sec.-butylphenyl) diphenyl phosphate, bis-(isopropylphenyl) phenyl phophate and bis-(sec.-butylphenyl) phenyl phosphate.

The phosphate esters are prepared by the reaction of the appropriate phenol or mixture of phenols with an ester-forming derivative of phosphoric acid. Phosphoric acid itself is not normally employed since the esterification is more readily carried out using phosphorus oxychloride, phosphorus pentoxide or phosphorus pentachloride. The reaction between a phenol and a chloride of metal halide catalyst such as aluminium chloride or magnesium chloride or other esterification catalyst such as an alkyl titanate ester. The use of such a catalyst allows completion of the reaction at much lower temperatures than are otherwise possible. The phosphate esters may also be prepared by a transesterification reaction carried out between a low-boiling trialkyl phosphate and the phenol or phenols, usually in the presence of a transesterification catalyst. Generally in any of these reactions a 2-5% molar excess of the phenol is employed over that required to react with the ester-forming derivative. The preferred reaction involves heating the phenol or phenols with phosphorus oxychloride slowly to a maximum temperature of about 160° C over a period of 6 to 10 hours. When phosphorus oxychloride is employed as one of the reactants, hydrogen chloride is evolved and may be absorbed in water in a suitable contacting chamber.

The triaryl phosphate mixture may be recovered from the reaction mixture by contacting or extracting the crude product with aqueous alkali to remove acidity and excess phenols, followed, if desired, by treatment with an oxidising agent to remove the oxidisable impurities. Alternatively, the mixture may be purified by distilling the crude product under reduced pressure to separate a main portion which is contacted or extracted with aqueous alkali and treated, if desired, with an oxidising agent.

The triaryl phosphates for present use are often advantageously employed in conjunction with a small amount, for instance up to 5% by weight of the plasticiser, of a bis-phenol or hindered phenol as antioxidant for the triaryl phosphate. By "bis-phenol" is meant a compound containing two separate hydroxy-substituted phenyl groups linked by an alkylene or sulphur bridge, and by a "hindered phenol" is meant a phenol wherein at least one, preferably both, of the positions ortho to the phenolic group are substituted. Such antioxidants are often employed in polyvinyl chloride compositions. but in the present case there is advantage in pre-mixing such antioxidant with the triaryl phosphate before the phosphate is supplied for blending with the vinyl chloride polymer at some later date in order to act as a plasticiser therefor.

The polymer compositions of the invention comprise a polymer of vinyl chloride and the said phosphate esters as plasticisers therefor in a compatible amount up to a maximum of 150 parts by weight of phosphate ester per 100 parts by weight of resin. The phosphate ester employed must be liquid at ambient temperature. The polymer of vinyl chloride may be polyvinyl chloride or a copolymer of vinyl chloride formed from not more than 20% of monomers other than vinyl chloride, for example vinylidene chloride and/or acrylonitrile. The phosphate esters may be employed as the sole plasticisers in the resin composition or they may be combined with other plasticisers, for example dialkyl esters of dicarboxylic acids such as dioctyl sebacate. The quantity of the plasticisers required will depend upon the nature and the desired properties of the resin composition. In plasticising polyvinyl chloride, the quantity of the present phosphate ester, when used alone, will normally range from 30 to 70% of the weight of the polyvinyl chloride or vinyl chloride copolymer.

The resin compositions may, of course, also comprise other conventional additives, particularly one or more heat or light stabilisers and/or antioxidants.

Though the novel phosphate esters of the invention have been described mainly for use as plasticisers, it is also envisaged that they may find use as lubricants or hydraulic fluids, particularly where it is desirable that such lubricants and fluids should be non-inflammable.

The invention is illustrated by the following Examples in which all quantities are expressed on a weight basis. Examples 1 to 3, 6 and 7 illustrate the preparation of the novel phosphate esters of the invention and Examples 4 to 7 illustrate the resin compositions of the invention wherein the improved low temperature flexibility of the compositions is illustrated by reference to the so-called cold-flex temperature as determined by the standard Clash and Berg Test, the lower the value of this temperature the better the cold temperature flexibility of the resin composition.

EXAMPLE 1

Phenol (65.2 parts) and a mixture of meta- and para-isopropyl phenols (47.9 parts) were mixed with phosphorus oxychloride (51 parts; that is a 5% excess of phenolic reactants). Powdered anhydrous magnesium chloride (0.5 part) was added to catalyse the reaction. The reaction mixture was rapidly heated to 130° C and then slowly to 230° C over a period of about 2 hours, after which there was no further appreciable evolution of hydrogen chloride. Completion of the reaction was checked by titration tests on the crude product which was then distilled under vacuum to give a fraction of recovered phenols, a small intermediate fraction and a main ester fraction (88% of crude product) boiling at 205°-225° C at 1 mm. of mercury.

The composition of the recovered phenolic fraction was shown by analysis to be substantially the same as that of the phenolic feedstock mixture, indicating that there had been no appreciable separation of the components due to preferential esterification. This was verified by hydrolysing a portion of the main ester fraction and analysing the recovered phenols. The distilled ester had a satisfactory colour, content of oxidisable impurities and acidity and was not therefore further purified. The viscosity of the product was 30 cs. at 25° C and the specific gravity (25° C/25° C) was 1.169. The constitution of the mixture was shown to be:

|  | mole-percent |
|---|---|
| Triphenylphosphate | 30 |
| Mono-(isopropylphenyl) diphenyl phosphate | 44 |
| Bis-(isopropylphenyl) phenyl phosphate | 22 |
| Tris-(isopropylphenyl) phosphate | 4 |
|  | 100 |

Thus the mixed phosphate esters had a calculated carbon number of 21 and containing 33 mole-percent of the isopropylphenyl group.

EXAMPLE 2

Phenol (32.6 parts) and a mixture of meta- and para-isopropyl phenols (95.8 parts) were mixed with phosphorus oxychloride (51 parts) and anhydrous magnesium chloride (0.6 part) as catalyst. Reaction and purification were carried out as in Example 1 and the main ester fraction (89% by weight of the crude product) distilled at 207–230° C. at 1 mm. of mercury. As in Example 1 the product required no further purification and had a viscosity of 58 cs. at 25° C. and a specific gravity (25° C./25° C.) of 1.123.

Analysis of the mixed ester indicated it to possess the following constitution:

|  | Mole-percent |
|---|---|
| Triphenyl phosphate | 4 |
| Mono-(isopropylphenyl) diphenyl phosphate | 19 |
| Bis-(isopropylphenyl) phenyl phosphate | 52 |
| Tris-(isopropylphenyl) phosphate | 25 |

The product therefore had a carbon number of 24 and contained 66 mole-percent of the isopropylphenyl group.

EXAMPLE 3

Diphenyl phosphochloridate (289 parts) and pyridine (30 parts) were mixed and a solution of para-capryl phenol (216 parts) in pyridine (100 parts) added during 2 hours. A reaction temperature of 25° C. was maintained by external cooling of the reaction mixture. Thereafter the reaction mixture was stirred for 6 hours at ambient temperature, and the precipitate of pyridine hydrochloride which had formed removed by filtration. The filtrate was washed successively with 5% hydrochloric acid and, 2% sodium hydroxide and then with water until neutral. Distillation at 223–229° C. at 1 mm. of mercury gave a mixed ester shown to consist of mono-(para-caprylphenyl) diphenyl phosphate (98%) and triphenyl phosphate (2%). Thus this product had a calculated carbon number of 26 and contained 33 mole-percent of the caprylphenyl group. The viscosity of the Phosphate ester product was 74 cs. at 25° C. and the specific gravity (25° C./25° C.) was 1.104.

EXAMPLE 4

A PVC formulation was prepared consisting of:

|  | Parts |
|---|---|
| Polyvinylchloride (a high molecular weight vinyl chloride homopolymer sold under the trade name BREON III | 100 |
| Phosphate ester plasticiser (as prepared in Example 1) | 82 |

| | Parts |
|---|---|
| White lead (as stabiliser) | 6 |

The formulation was milled on a 2-roll mill for 7 minutes at 165° C and then pressed into a sheet of uniform thickness. The Clash and Berg cold flex temperature of the sheet was −21° C as compared to −11° C for a comparative sheet wherein the same amount of tricresyl phosphate was employed as plasticiser and −8.5° C for a similar comparative sheet wherein the plasticiser was trixylyl phosphate.

EXAMPLE 5

Example 4 was repeated but employing as the plasticiser the phosphate ester as prepared in Example 2. The cold flex temperature of the resulting PVC sheet was −20.3° C.

EXAMPLE 6

A plasticiser was prepared by reacting one molar proportion of diphenyl phosphorochloridate with one molar proportion of a mixture consisting substantially of meta- and para-sec.-heptyl phenols in an exactly analogous manner to that given in Example 3 to give a phosphate ester of carbon number 25. This was used to prepare a PVC sheet as in Example 4, the cold flex temperature of which was −22° C. The cold flex temperature of a PVC sheet similarly prepared from a coal tar phenol phosphate ester having a carbon number of 25 was −7° C.

EXAMPLE 7

A plasticiser was prepared in a manner analogous to Example 3 by reacting one molar proportion of diphenyl phosphorochloridate with one molar proportion of a mixture of meta and para secondary butyl phenols to give a phosphate ester of carbon number 22. This was used to prepare a PVC sheet, as in Example 4, the cold flex temperature of which was −21° C.

What is claimed is:

1. A composition consisting essentially of a liquid mixture of a plurality of phenyl alkylphenyl phosphates having the overall general formula $(RO)_3PO$ wherein R is selected from the group consisting of phenyl and secondary alkylphenyl groups, and from 30 to 85 mole percent of the R groups are secondary alkylphenyl groups and the secondary alkyl group has from 3–4 carbon atoms, said mixture being prepared by phosphorylating a mixture of phenol and at least one alkylphenol ROH wherein R is alkylphenyl as defined hereinbefore.

2. The composition of claim 1 wherein up to 70 mole-percent of the R groups are secondary alkylphenyl groups.

3. The composition of claim 2 wherein said secondary alkylphenyl groups are isopropylphenyl groups.

4. The composition of claim 2 wherein the alkylphenyl groups are isopropylphenyl groups and the ratio of isopropylphenyl groups to phenyl groups is about 1 to 2.

5. The composition of claim 2 wherein the alkylphenyl groups are isopropylphenyl groups and the ratio of isopropylphenyl groups to phenyl groups is about 2 to 1.

6. The composition of claim 2 wherein said isopropylphenyl groups are predominantly meta-isopropylphenyl groups.

7. The composition of claim 2 wherein said secondary alkylphenyl groups are sec-butylphenyl groups.

8. The composition of claim 2 wherein the alkylphenyl groups are sec.-butylphenyl groups and the ratio of sec.-butylphenyl groups to phenyl groups is about 1 to 2.

9. The composition of claim 2 wherein the alkylphenyl groups are sec.-butylphenyl groups and this ratio of sec.-butylphenyl groups to phenyl groups is about 2 to 1.

10. The composition of claim 2 wherein said sec.-butylphenyl groups are predominantly meta-sec.-butylphenyl groups.

11. A composition consisting essentially of a liquid mixture of triaryl phosphate esters wherein the aryl groups of said esters are phenyl and isopropylphenyls, wherein between 20 and 70 mole-percent of said aryl groups are said isopropylphenyls, said mixture being prepared by phosphorylating a mixture of phenol and isopropylphenols.

12. The composition of claim 11 wherein the ratio of isopropylphenyl groups to phenyl groups is about 1 to 2.

13. The composition of claim 11 wherein the ratio of isopropylphenyl groups to phenyl groups is about 2 to 1.

14. The composition of claim 11 which contains triphenylphosphate, mono-(isopropylphenyl)diphenylphosphates, bis-(isopropylphenyl)phenylphosphates, and tris-isopropylphenyl)phosphates.

15. The composition of claim 14, wherein the ratio of the isopropylphenyl groups to the phenyl group is about 1:2.

16. The composition of claim 14, wherein the ratio of the isopropylphenyl groups to the phenyl group is about 2:1.

17. A liquid mixture of phosphates having the overall general formula $(RO)_3PO$ wherein R is selected from the group consisting of phenyl and isopropylphenyl groups and from 30 to 85 mole percent of the R groups are isopropylphenyl groups, said mixture consisting essentially of triphenylphosphate, mono-(isopropylphenyl)diphenylphosphates, bis(isopropylphenyl)phenylphosphates, and tris-(isopropylphenyl)phosphates.

18. The liquid mixture of claim 17, wherein the ratio of the isopropylphenyl groups to the phenyl group is about 1:2.

19. The liquid mixture of claim 17, wherein the ratio of the isopropylphenyl groups to the phenyl group is about 2:1.

* * * * *

UNITED STATES PATENT AND TRADEMARK OFFICE
CERTIFICATE OF CORRECTION

PATENT NO. :   4,139,487
DATED      :   February 13, 1979
INVENTOR(S) :  KENNETH M. GARRETT It is certified that error appears in the above—identified patent and that said Letters Patent is hereby corrected as shown below:

Column 3, line 18:  rewrite "phophate" as --phosphate--.

Column 5, line 9:   between the numerals "4" and "100", insert a horizontal line.

Column 5, line 11:  rewrite "containing" as --contained--.

Column 7, line 12:  (Claim 9) rewrite "this" as --the--.

Column 8, line 7:   (Claim 14) rewrite "tris-isopropylphenyl) phosphates" as --tris-(isopropylphenyl)phosphates--.

Signed and Sealed this

Twenty-first Day of April 1981

[SEAL]

Attest:

RENE D. TEGTMEYER

*Attesting Officer*    *Acting Commissioner of Patents and Trademarks*